DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JANUARY 20, 1970

870 O.G. 727

T870,015
ODOR CONTROL PROCESS

Bobby N. Scoggins and John W. Thompson, both of P.O. Box 511, Kingsport, Tenn. 37662

Filed Sept. 18, 1967, Ser. No. 668,677
Int. Cl. D21c *11/08*
U.S. Cl. 162—51
No Drawing. 8 Pages Specification

The reduction of odors generated in cellulosic digestion processes, such as in the Kraft process, by adding thereto a compound having the formula

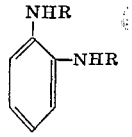

wherein R is a straight or branched alkyl radical of 3–12 carbons.